United States Patent [19]

Hsiao

[11] Patent Number: 5,563,981
[45] Date of Patent: Oct. 8, 1996

[54] ELECTRIC GLASS INCENSE BURNER STRUCTURE AND HEAT CONDUCTING DEVICE THEREOF

[76] Inventor: Ming Jen Hsiao, No. 909, Chien Fong Rd., Tou Feng, Miao Li, Taiwan

[21] Appl. No.: 416,232

[22] Filed: Apr. 4, 1995

[51] Int. Cl.⁶ .............................. F24F 3/14; F27D 11/00; H05B 3/44
[52] U.S. Cl. .......................... 392/402; 219/385; 219/436; 219/544
[58] Field of Search ....................... D11/131.1; 219/385, 219/401, 402, 408, 436, 438; 392/386, 402

[56] References Cited

U.S. PATENT DOCUMENTS

| | | | |
|---|---|---|---|
| 1,975,082 | 10/1934 | Bucy | 392/386 |
| 2,538,977 | 1/1951 | Mucher | 219/544 |
| 4,148,250 | 4/1979 | Miki et al. | 219/436 |
| 4,280,046 | 7/1981 | Shimoturi et al. | 219/544 |

Primary Examiner—Teresa J. Walberg
Assistant Examiner—Sam Paik
Attorney, Agent, or Firm—Pro-Techtor International

[57] ABSTRACT

An improved electric glass incense burner structure having a heat conducting device, wherein on a lid thereof perfume emitting holes and a spherical knob are provided. The burner housing on its wall a pair of protruding pillars for supporting a clamping sheet. A heat conducting device is in close contact with the bottom of the burner for uniform and fast heat conducting.

2 Claims, 5 Drawing Sheets

ELECTRIC GLASS INCENSE BURNER STRUCTURE AND HEAT CONDUCTING DEVICE THEREOF

BACKGROUND OF THE INVENTION

1. Field of the Invention

The present invention relates to an improved electric glass incense burner and a heat conducting device used therein.

2. Description of the Prior Art

An electric incense burner takes advantage of electric conduction to emit perfumed air. The air emitted is aromatic as well as clean. However, such electric incense burners are usually made of ceramic material, and thus has the following practiced disadvantages. (Please refer to FIG. 2).

1. The knob A2 on the lid A is made as a smooth column. It can inadvertently slip out of a user's hand when it is moist, and fall to the ground and be broken.

2. The lower part of the burner B has a bottom B1 which protrudes upward to create a cavity in which to fix a heating device. The fragility of the ceramic material makes the bottom part weakened. Moreover, a lip M extends under the bottom B1 to hold a clamping sheet L and a base C. A user must take care not to lock the base C and the conducting plate D too tightly. Otherwise, the bottom B1 is subject to cracking and the lip M can be broken. Moreover, the heat conducting effect of this burner is not optimal because the conducting plate D is fixedly attached to the central portion of the protruding bottom B1, thereby leaving the surrounding portion of the burner out of the contact with the heating device.

3. Because the incense burner B is produced by burning ceramic material, power may be wasted in construction.

The structure of a conventional heat conducting device, such as is shown in FIGS. 1 and 2, is constructed to have a metallic bottom plate E. a lower mica slice F. a middle mica slice G. and an upper mica slice H. etc. which are lapped and rivetted together. The middle mica slice G is wound with nickel and chromium wire G1. Both ends of the nickel and chromium wire G1 are connected by a pair of terminals I1 to conductors I which are connected to a switch and a plug. In such a heat conducting device, the upper mica slice H is fixed to the bottom B1 of the electric incense burner. The metallic bottom plate E is fixed to the bottom B1 of the electric incense burner B with a bolt J and a nut K and a clamping sheet L. The high heat produced in the nickel and chromium wires G1 after turning on the electricity is transmitted to the bottom B1 of the burner B through the upper mica slice H. However, such a conventional heat conducting device has the following defects due to its structure:

1) The metallic bottom plate E in the heat conducting device is conductive. Often, when the electric incense burner B is broken accidentally, or when water permeates into the bottom layer of the burner B, electric leakage can occur. Thus, users are subjected to the risk of electric shock.

2) The avoid losing heat efficiency, the heating power should be adapted to the length of the nickel and chromium wire, e.g., if 25 W heat energy ( 110 volts) is to be produced, the length of the nickel and chromium wire should be 500 mm. the nickel and chromium wire of the prior art heat conducting device is would by hand. Thereby allowing significant differences in lengths of the nickel and chromium wires. Inconsistent width of the turns of each nickel and chromium wire wound on the mica slice, or too large spaces between the wires, reduces the heating efficiency.

3) Resistance to high pressure of the metallic bottom plate E is inferior, and it will not pass the high pressure safety test of American UL (standard value is 1,500 v).

SUMMARY OF THE INVENTION

In view of these shortcomings of the prior art, the present invention provides improvements of the conventional electric incense burner and heat conducting device. The present invention uses a novel electric glass incense burner with a heat conducting device, utilizing stable heating power, high heating efficiency, and good insulation. The defects of the conventional electric incense burner can thus be surely and effectively eliminated, and safety of use, beauty of appearance, and high efficiency of heat conduction can be achieved.

The present invention will be apparent in its practical structure, characteristics, and functions after reading the detailed description of the preferred embodiment thereof with reference to the accompanying drawings.

DETAILED DESCRIPTION OF THE PREFERRED EMBODIMENT

Figure 1:
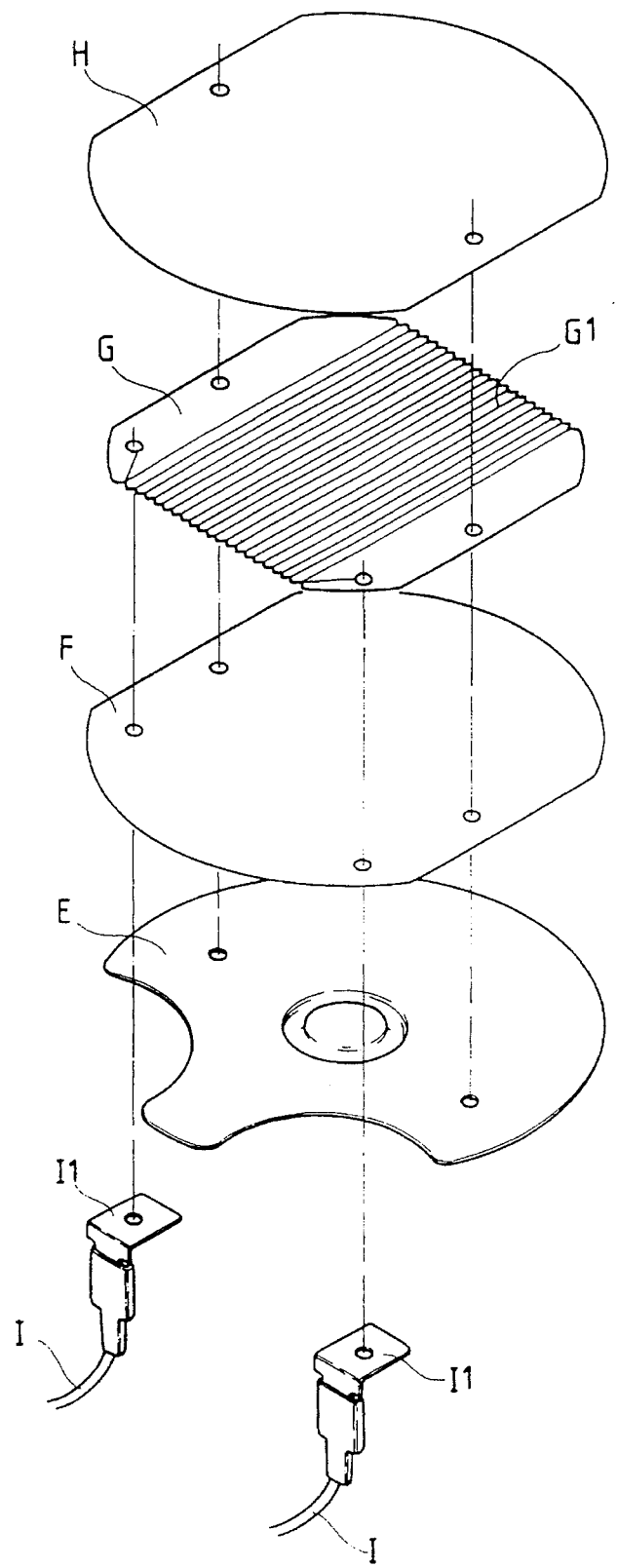
FIG. 1 is an exploded view of a conventional heat conducting device for an electric incense burner.
Figure 2:
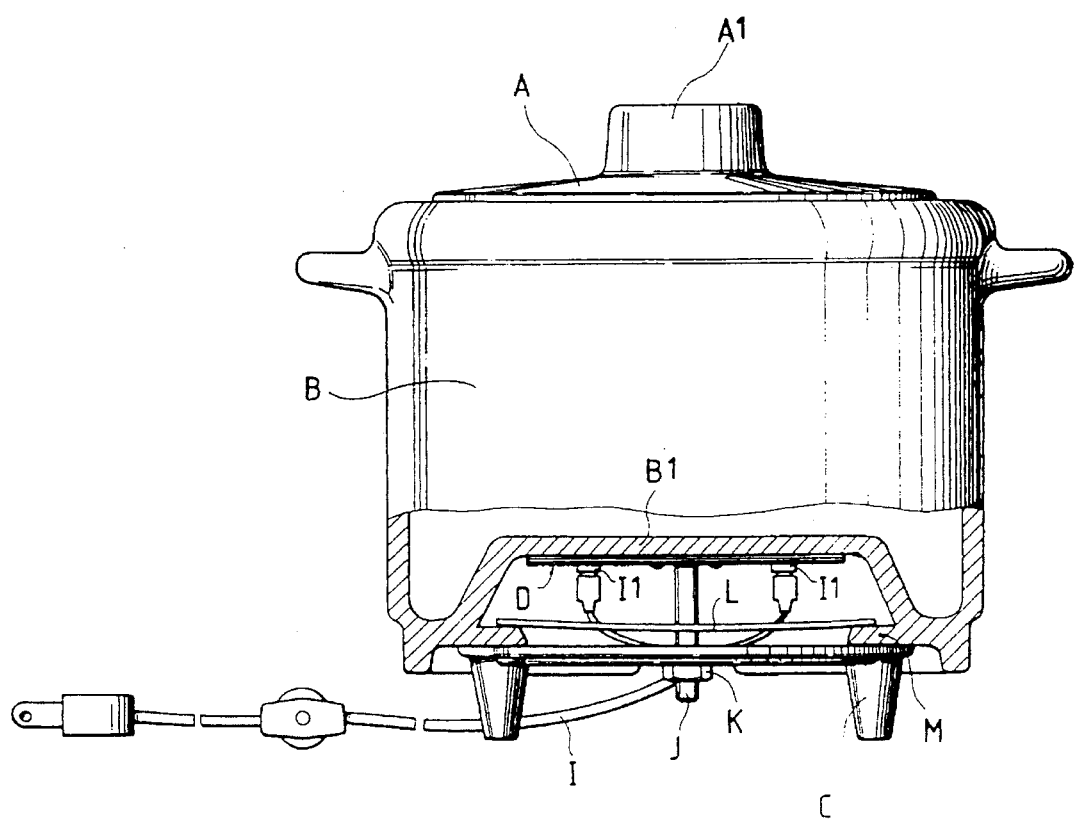
FIG. 2 is a partial cross section view showing the assembly of the conventional heat conducting device for an electric incense burner.
Figure 3:
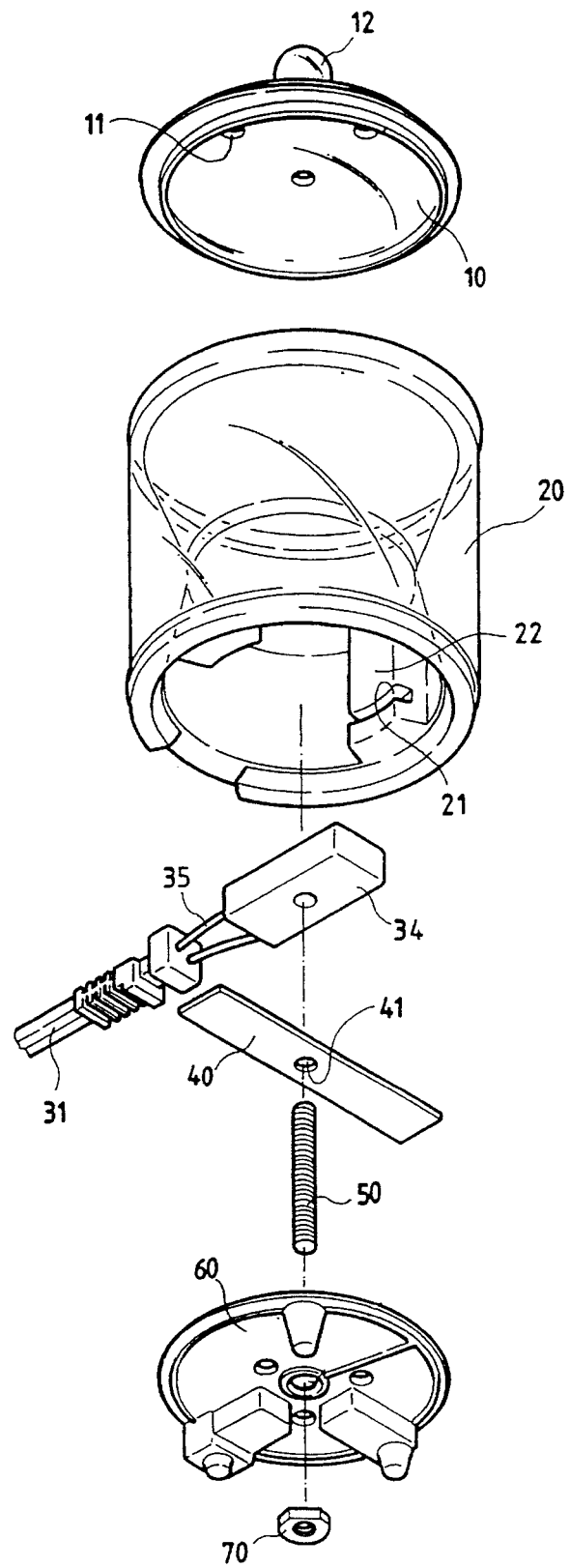
FIG. 3 is an exploded view of the present invention.
Figure 4:
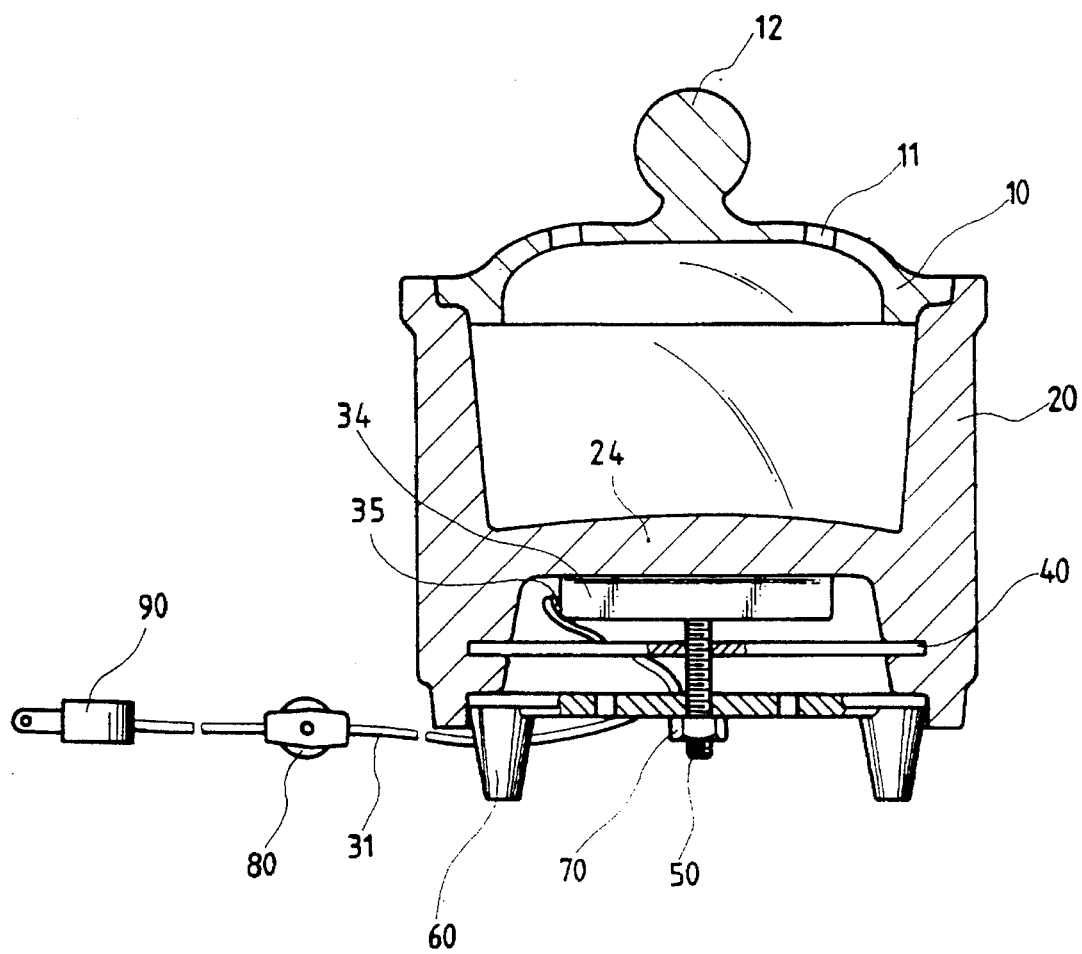
FIG. 4 is a sectional view showing the structure of the present invention when it is assembled.

Referring to FIGS. 3 and 4, the electric glass incense burner housing 20 of the present invention is integrally formed from crystal glass. The burner housing 20 has the quality of high temperature resistance, high transparency, and heat conductivity which is far greater than that of ceramic material. A plurality of perfume emitting round holes 11 are provided on a lid 10. A spherical knob 12 is provided on top of the lid 10, and has a beautiful appearance as well as practical value of use. The lower part of the knob 12 is connected with the lid 10. Such design is beneficial to a user's grip, and the lid will therefore not easily slip from the user's hand. The space beneath the burner housing 20 of the present invention has on its wall a pair of symmetrically arranged protruding pillars 22 in which are provided two slots 21 for receiving a clamping sheet 40. The bottom 24 of the burner housing 20 arcs slightly upward, so that the heat conducting face on the conducting device will have maximum contact with the bottom 24 of the electric incense burner housing 20, so as to have uniform and fast heat conduction. The burner housing 20 and the lid 10 are both transparent, so the user can see at any time whether the essence inside has been volatilized.

Figure 5:
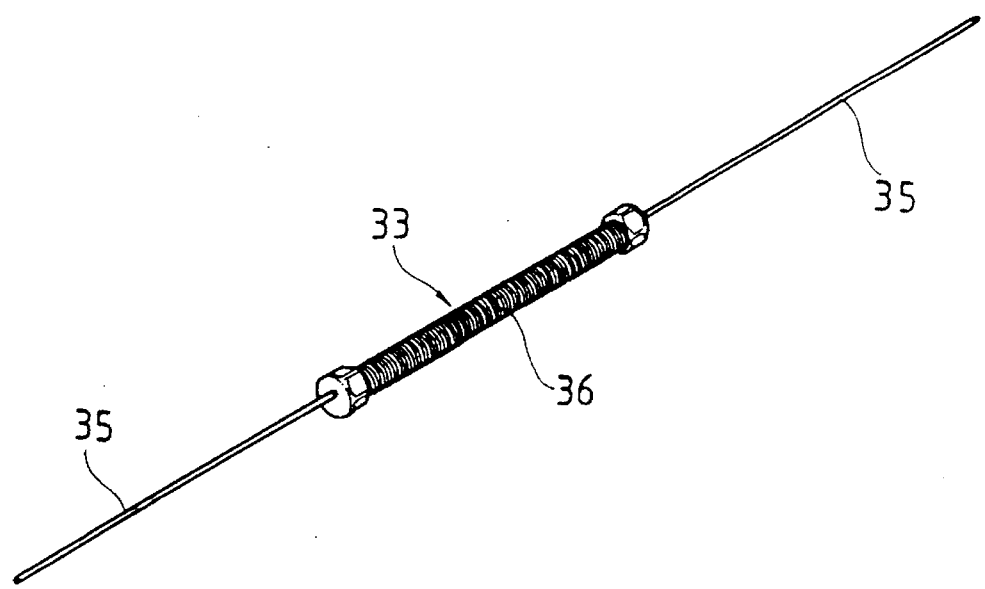
FIG. 5 is a perspective view of a heat conducting bar.
Figure 6:
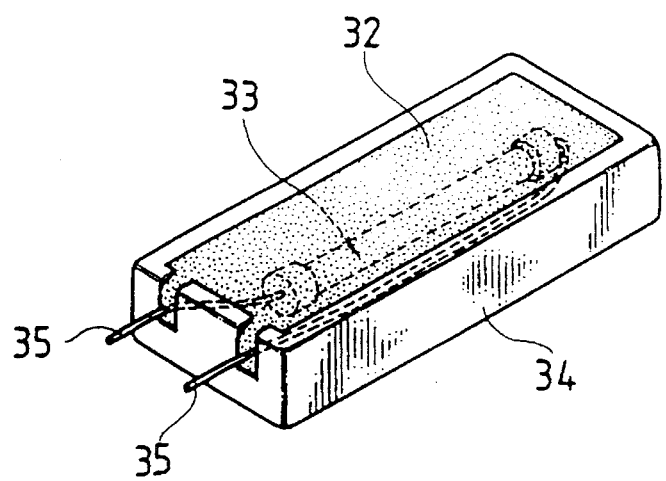
FIG. 6 is a perspective view of the heat conducting device of the present invention.

Referring now to FIGS. 5 and 6, the heat conducting device includes mainly an FRP stick 33 (having on each end thereof a conductive terminal 35), and tightly wound nickel and chromium wire 36 of the length which can exactly achieve the heating power desired. Both ends of the nickel and chromium wire 36 connect respectively with the two conductive terminals 35 to form a heat conducting bar. As shown in FIG. 6, the heat conducting bar has its terminals 35 bent and extended to one end. The bar is placed in a ceramic housing 34 and wrapped in an aluminum oxide covering 32 to form a heat conductive device having a heat conducting face on the top of the ceramic housing 34. The terminals 35 of the heat conducting device extend out from the ceramic housing 34 as shown in FIG. 6. As shown in FIG. 4, the terminals 35 connect wit ha conductor 31 which in turn connects with a switch 80 and a plug 90. Referring again to FIGS. 3 and 4, the present invention has its heat conducting face of the ceramic housing 34 in contact with the bottom 24 of the electric incense burner housing 20. The clamping sheet 40 is firmly held in the two slots 21 of the protruding pillars 22. Moreover, a bolt 50 is screwed in a screw hole 41 provided on the clamping sheet 40 to tightly abut against the ceramic housing 34. A nut 70 is used to lock a base 60 onto the electric incense burner housing 20 from below. The pair of pillars 22 protrude from the wall of the electric incense burner housing 20 and extend in the space under the burner housing 20, to provide a thick receiving from the clamping sheet to be locked into. There is therefore no breaking or cracking like the lip M or the bottom B1 of the conventional electric incense burner.

When the plug 90 of the conductor 31 is inserted into an electrical socket and the switch 80 is turned on to heat the nickel and chromium wire 36, heat is transmitted into the electric incense burner housing 20 to volatilize the incense and thus to emit fragrance throughout the indoor space.

The design of the present invention provides the following effects:

1. Since the electric glass incense burner housing 20 is transparent, a user can observe whether the essence inside has been volatilized. The transparent burner is also aesthetically pleasing.
2. A pair of pillars 22 having slots 21 protrude from the wall of the electric incense burner housing 20 and provide a thick area for the locking operation. No breaking or cracking will occur as it can in the conventional electric incense burners.
3. The design of a spherical knob 12 is provided on the lid 10 not only has a beautiful appearance, but also is beneficial to gripping thereof.
4. The glass incense burner housing 20 and a heat conducting device of the present invention are more heat efficient than prior art devices.
5. The heat conducting bar is wholly surrounded by a ceramic housing 34, and wrapped in aluminum oxide, providing excellent heat insulation and high temperature resistance. Even when the electric incense burner housing 20 is broken, or when water permeates into the bottom layer of the burner housing 20, no electric leakage will occur. Thus users are not subjected to electric shock.
6. A tightly wound nickel and chromium wire 36 of the length which is accurately controlled (wound with a machine) has stable heating power and concentrated heat energy. It is excellent in heat conducting, and costs of electrical power can be reduced.
7. Ceramic material and aluminum oxide have high pressure resistance, and can therefore pass the high pressure safety test of American UL.

Accordingly, the novel structural design of the present invention not only effectively eliminates the shortcomings of the heat conducting device of a conventional electric incense burner, but also has the above mentioned effects as to safety and efficiency of energy utilization.

I claim:

1. An electric glass incense burner comprising:

a glass burner housing, a lid with a plurality of perfume emitting round holes and a spherical knob, a space at a lower end of said housing has on an inner wall a pair of protruding pillars in which are provided two slots to receive a clamping sheet, the bottom of said burner housing arcs slightly upward such that a heat conducting face on a heat conducting device contacts said bottom of said burner housing, a bolt is screwed in a screw hole provided on said clamping sheet to tightly abut against said heat conducting device, a nut is used to lock a base onto said burner housing from below; and said heat conducting device includes a heat conducting bar and a ceramic housing.

2. The electric glass incense burner as claimed in claim 1, wherein:

said heat conducting device includes an FRP stick having on each end thereof a conductive terminal, and a tightly wound nickel and chromium wire of suitable length, both ends of said nickel and chromium wire connect respectively with said two conductive terminals to form a heat conducting bar, said heat conducting bat is enclosed in a ceramic housing and covered with aluminum oxide to form a heat conducting face of said heat conducting device on a top of said ceramic housing, said terminals each extend outward from one end of said ceramic housing and connect with a conductor.

\* \* \* \* \*